United States Patent [19]
Schulte-Elte

[11] 3,937,723
[45] Feb. 10, 1976

[54] CYCLOALIPHATIC COMPOUNDS AS ODOUR- AND TASTE-MODIFYING AGENTS

[75] Inventor: Karl-Heinrich Schulte-Elte, Onex, Geneva, Switzerland

[73] Assignee: Firmenich S.A., Geneva, Switzerland

[22] Filed: Jan. 25, 1974

[21] Appl. No.: 436,786

[30] Foreign Application Priority Data
Feb. 9, 1973 Switzerland.......................... 1941/73

[52] U.S. Cl............ 260/488 R; 131/17 R; 252/522; 260/340.9; 260/468 L; 260/491; 260/598; 260/611 R; 260/617 C; 260/617 R; 260/999; 426/538
[51] Int. Cl.²................ C07C 69/07; C07C 69/145; C07C 69/24
[58] Field of Search..................... 260/488 R, 617 R

[56] References Cited
UNITED STATES PATENTS
2,934,560  4/1960  Kimel............................ 260/488 R
3,381,017  4/1968  Waugh............................ 260/617 R
3,743,671  7/1973  Teisseire et al................. 260/488 R OTHER PUBLICATIONS
Chem. Abstracts, 71:10202/r.
Chem. Abstracts, 79:18867d.

Primary Examiner—Vivian Garner
Attorney, Agent, or Firm—Pennie & Edmonds

[57] ABSTRACT

New cycloaliphatic compounds useful as perfuming and odour-modifying agents in the manufacture of perfumes and perfumed products, and as flavouring and taste-modifying agents in the aromatization of foodstuffs in general and imitation flavours for foodstuffs, beverages, animal feeds, pharmaceutical preparations and tobacco products.

Novel process for the preparation of said cycloaliphatic compounds and compositions of matter relating to mixtures containing same.

9 Claims, No Drawings

CYCLOALIPHATIC COMPOUNDS AS ODOUR- AND TASTE-MODIFYING AGENTS

SUMMARY OF THE INVENTION

The compounds to which the present invention relates belong to the class of cycloaliphatic derivatives having the formula

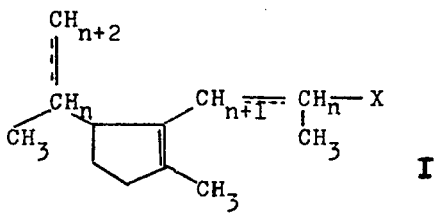

containing a single or double bond in the positions indicated by the dotted lines and wherein:

$n$ stands for 0 or 1; and

X represents a univalent radical of formula
(a) —CHO; (b) -CH-OR; OR
(c) —CH$_2$OR$^1$ or (d) -CH-O O-(CH$_2$)$_2$ wherein R is an alkyl radical containing from 1 to 6 carbon atoms, and R$^1$ represents a hydrogen atom or an acyl radical containing from 1 to 6 carbon atoms.

The said compounds possess interesting organoleptic properties and accordingly represent useful perfuming and odourmodifying agents as well as flavouring and taste-modifying agents in their own right. They equally represent useful intermediates for the preparation of other compounds having valuable fragrant and flavouring character.

The present invention relates further to novel perfume and flavouring compositions, as well as to certain perfumed and flavoured articles.

This invention equally provides a process for the preparation of the compounds of formula I.

PREFERRED EMBODIMENTS OF THE INVENTION

We have discovered that in view of their particular useful properties, the novel compounds of the present invention can be used for modifying, enhancing or improving the organoleptic properties of foodstuffs, animal feeds, beverages, pharmaceutical preparations and tobacco products and for the manufacture of artifical flavouring compositions.

The term "foodstuff" is here used broadly and includes, for example, coffee, tea or chocolate.

Typically, the compounds of formula I develop various flavour notes such as green, fruity and flowery notes. Depending on the nature of the other constituents in a given composition or on that of the materials to which they are added, the compounds of formula I can develop certain notes reminiscent of fruits such as melon or cucumber.

These flavouring characters provide a particular useful application for the aromatization of beverages, e.g. fruit juices, jams, yoghurts, milk products, confectionery and bakery articles. The compounds of the invention equally find a useful application for the aromatization of decoctions or infusions, camomile, lime-blossom tea or verbena.

Typically, interesting flavouring effects can be achieved with amounts ranging from 0.5 to 50 ppm, based on the weight of the product flavoured. However, in order to achieve special effects, this amount can be raised to about 100 or even 1000 ppm. When compounds I are used in flavouring compositions, in admixture with other flavouring agents, they may typically comprise from 1 to about 20% of the total weight of the composition.

Further, the compounds of formula I possess interesting olfactive properties and, accordingly, can be used in the art of perfumery. They impart a variety of fragrance notes such a minty, grass-like, green, aromatic, amber-like, camphoraceous or ambrette-like notes. Their aromatic character is reminiscent of the odour of certain plants belonging to the family of labiates, marjoram in particular. Accordingly, the compounds of formula I are particularly useful for the preparation of fragrant compositions of floral type. The well developed ambrette-like character of certain of the mentioned compounds, enables their use in fine perfumery for exalting the overall odoriferous effect of perfume compositions. Some of the compounds of formula I, the 2-methyl-3-(2-methyl-5-isopropenyl-cyclopent-1-en-1-yl)-propyl acetate in particular, show the interesting properties of increasing the diffusiveness and richness of the fragrances in which they are incorporated. 2-Methyl-3-(2-methyl-5-isopropenyl-cyclopent-1-en-1-yl)-propyl acetate possesses the useful and interesting property of developing a woody, ambrette-like fragrance of a very tenacious character. These properties render the said compound particularly suitable for a great variety of applications in the field of fine perfumery as well as in the perfuming of soaps. In view of the wide application of natural ambrette seeds oil in the art, perfumers were always concerned about finding new possible cheap synthetic substitutes for it. The present invention represents a solution to this problem and enables the man in the art to enlarge the palette of useful synthetic materials put to his disposal.

It is an object of the present invention to provide perfume compositions comprising olfactive amounts of at least one of the compounds of formula I.

It is a further object of the present invention to provide perfumed articles comprising as odour modifying agent at least one of the compounds of formula I.

The term "perfume composition" is used herein to mean a mixture of organic compounds including, for example, alcohols, aldehydes, ketones, esters and hydrocarbons which are admixed in a manner and in quantity ranges usual in the art. Perfumed articles include a variety of materials, for example, cosmetics, washing powders, cleaning agents, soaps, shampoos, talc, waxes and house-hold articles in general.

Compounds I are equally useful for the reconstitution of certain artificial essential oils, floral essential oils for example.

Typically, interesting odoriferous effects can be obtained when the compounds of formula I constitute from about 0.5 to 5 percent by weight of the total composition; but, depending on the effect required, the proportion of compounds I may be increased to 20 percent by weight, or even more. The proprotions can be much lower when the compounds of formula I are incorporated into materials such as soaps or detergents, for example. In all cases, the ranges mentioned above may be varied in order to achieve specific organoleptic effects. The examples which appear hereinbelow illustrate certain flavouring and perfume compositions within the scope of the invention. It has to be understood however that the given compositions represent preferred examples and the invention is not to be considered as restricted thereto.

Specific examples of the compounds defined by formula I include the following new compounds:

2-methyl-3-(2-methyl-5-isopropenyl-cyclopent-1-en-1-yl)-propanal,
2-methyl- 3-(2-methyl-5-isopropyl-cyclopent-1en-1-yl)-propanal,
2-methyl-3-(2-methyl-5-isopropenyl-cyclopent-1-en-1-yl)-propanol,
2-methyl-3-(2-methyl-5-isopropenyl-cyclopent-1-en-1-yl)-propyl acetate;
2-methyl-3-(2-methyl-5-isopropyl-cyclopent-1-en-1-yl)-propanol,
2-methyl-3-(2-methyl-5-isopropyl-cyclopent-1-en-1-yl)-propyl acetate,
2-methyl-3-(2-methyl-5-isopropenyl-cyclopent-1-en-1-yl)-propanal-dimethylketal,
2-methyl-3-(2-methyl-5isopropyl-cyclopent-1en-1-yl)-1-ethylenedioxy-propane,
2-methyl-3-(2-methyl-5-isopropyl-cyclopent-1-en-1-yl)-propanal-dimethylketal,
2-methyl-3-(2-methyl-5-isopropyl-cyclopent-1-en-1-yl)-1-ethylenedioxy-propane,
2-methyl-3-(2-methyl-5-isopropenyl-cyclopent-1-en-1-yl)-propyl formate,
2-methyl-3-(2-methyl-5-isopropyl-cyclopent-1-en-1-yl)-propyl formate,
2-methyl-3-(2-methyl-5-isopropyl-cyclopent-1-en-1-yl)-prop-2-enol,
2-methyl-3-(2-methyl-5-isopropyl-cyclopent-1-en-1-yl)-prop-2-enyl acetate and
2-methyl-3-(2-methyl-5-isopropyl-cyclopent-1-en-1-yl)-prop-2-enal.

One of the compounds of this invention, specifically 2-methyl-3-(2-methyl-5-isopropyl-cyclopent-1-en-1-yl)-propanal, can be prepared by a novel process which comprises catalytically hydrogenating 2-methyl-3-(2-methyl-5-isopropenylcyclopent-1-en-1-yl)-propanal.

The reducing agents commonly known to promote the conversion of ethylenic double bonds into simple bonds, such as metals like platinum, palladium or rhodium, may be advantageously used. Platinum is preferably used in its oxidized form as $PtO_2$, whereas palladium is used on an inert support of charcoal or calcium carbonate (see for example: H. O. House, Modern Synthetic Reactions, W. A. Benjamin Inc., New York (1965), p. 1 and ff.). Raney nickel can equally be used; in this case however it is difficult to suppress the concomitant reduction of the aldehydic group.

In accordance with a preferred embodiment of the process of this invention, the catalytic hydrogenation of 2-methyl-3-(2-methyl-5-isopropenyl-cyclopent-1-en-1-yl)-propanal is effected in an inert organic solvent, e.g. an ether, such as dioxan, an aliphatic, cycloaliphatic or aromatic hydrocarbon, such as hexane, cyclohexane, benzene or toluene, a secondary or tertiary alcohol, such as isopropanol or terbutanol.

In accordance with a further object of the present invention, 2-methyl-3-(2-methyl-5-isopropenyl-cyclopent-1-en-1-yl)-propanal, used as starting material in the hereinabove described process, is prepared according to a process which comprises a thermal cyclization of 2,6-dimethyl-oct-2-en-7-yn-6-ol followed by an addition, on the methylenic double bond of the obtained compound, of ethoxy-prop-1-ene in the presence of catalytic amounts of an acidic agent. The hereinabove process is illustrated by the following reaction scheme:

Scheme I

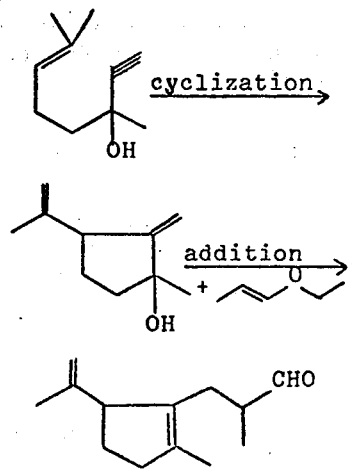

2,6,-Dimethyl-oct-2-en-7-yn-6-ol, used as starting material in the above process, is a commercial product better known under the name of dehydrolinalol.

The described process can be carried out with known techniques [cf. e.g.: German Pat. Nos. 1,082,257 and 1,193,490].

Thus, the said cyclization can be carried out at temperatures of 100° to 300°C, preferably of 180° to 250°C, and the addition of ethoxy-prop-1-ene at temperatures of 120° to 200°C, preferably of about 130° and 170°C. The given temperatures afford good reaction rates while minimizing undesirable reactions.

The said addition is effected in the presence of an acidic agent. Suitable acidic agents include a mineral protic acid, sulphuric or phosphoric acid for example, or an organic protic acid such as trichloracetic or p-toluenesulphonic acid. Lewis acids such as $BF_3$, $AlCl_3$ or $ZnCl_2$ can equally be used.

It will be appreciated that the given structure of the compounds of formula I includes various stereoisomeric forms.

For instance, due to the simultaneous presence of a hydrogen atom, a methyl group and an aldehydic radical on the carbon atom in position 2 of the molecule, the various isomeric forms of 2-methyl-3-(2-methyl-5-isopropyl-cyclopent-1-en-1-yl)-propanal can be represented by the following general formula

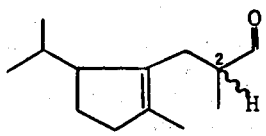

The said isomers can be used individually or in admixture with each other. They can be separated from each other by conventional techniques, such as vapour phase chromatography or fractional distillation by means of a spinning band column. For all practical purposes however, it is preferred to use the mixture of isomers as directly obtained by the process of the invention.

The saturated and unsaturated propanals, obtained in accordance with the process of the present invention, which possess useful properties on their own, equally represents useful intermediates for the preparation of the other members of the class of compounds defined by formula I. Thus, by reduction according to conventional techniques [cf.: H. O. House, Modern Synthetic Reactions, Benjamin Inc., (1965), p. 23 and ff.], 2-methyl-3-(2-methyl-5-isopropenyl-cyclopent-1-en-1-yl)-propanal can be converted into its corresponding hydroxylic derivative of formula

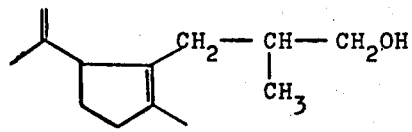

The following reaction scheme illustrates in a more detailed manner some of the chemical conversions to which the above mentioned aldehydes may undergo (see scheme II on the following page).

2-Methyl-3-(2-methyl-5-isopropyl-cyclopent-1-en-1-yl)-prop-2-enol and its corresponding acetate and aldehyde were prepared in accordance with techniques usual in the art as indicated by the following Examples (see particularly Example 3).

The invention is better illustrated by the following Examples, wherein the temperatures are indicated in degrees centigrade and the abbreviations used throughout have the meaning usual in the art.

EXAMPLE 1

2-Methyl-3-(2-methyl-5-isopropenyl-cyclopent-1-en-1-yl)-propanal a)

1-methyl-2-methylene-3-isopropenyl-cyclopentan-1-ol 1 kg of 2,6-dimethyl-oct-2-en-7-yn-6-ol was pyrolyzed during 12 hours at a temperature of about 180° under nitrogen atmosphere. There was thus obtained with 95% of yield a mixture comprising 55 : 45 parts by weight of the 2 diastereoisomers of the desired alcohol.

The time required for carrying out the pyrolysis can be drastically reduced by effecting the reaction at a higher temperature. Thus at temperatures of about 350° the reaction time can be reduced to about 0.5–1 second while obtaining the same or nearly the same yields.

The two said isomers showed the following analytical data:

A:
Bp. 35°–6°/0.2 Torr; $n_D = 1.4839$; $d^{20} = 0.9294$
IR: 3400, 3080, 1640, 895, 890 cm$^{-1}$
NMR: 1.33 (3H, s); 1.6 (3H, s); 4.75 (2H, m); 4.75 and 5.1 (3H, 2d, J=3 cps) δ ppm
MS: M$^+$ = 152 (1); m/e = 137 (32); 49 (24); 109 (37); 95 (53); 79 (63); 67 (38); 53 (17); 43 (100); 27 (20).

B:
Bp. 38°–9°/0.2 Torr; $n_D = 1.4811$; $d^{20} = 0.9247$
IR: 3400, 3080, 1800, 1640, 890 cm$^{-1}$
NMR: 1.26 (3H, s); 1.61 (3H, s); 4.73 (2H, m); 4.75 and 5.15 (2H, 2d, J=3 cps) δ ppm Scheme II

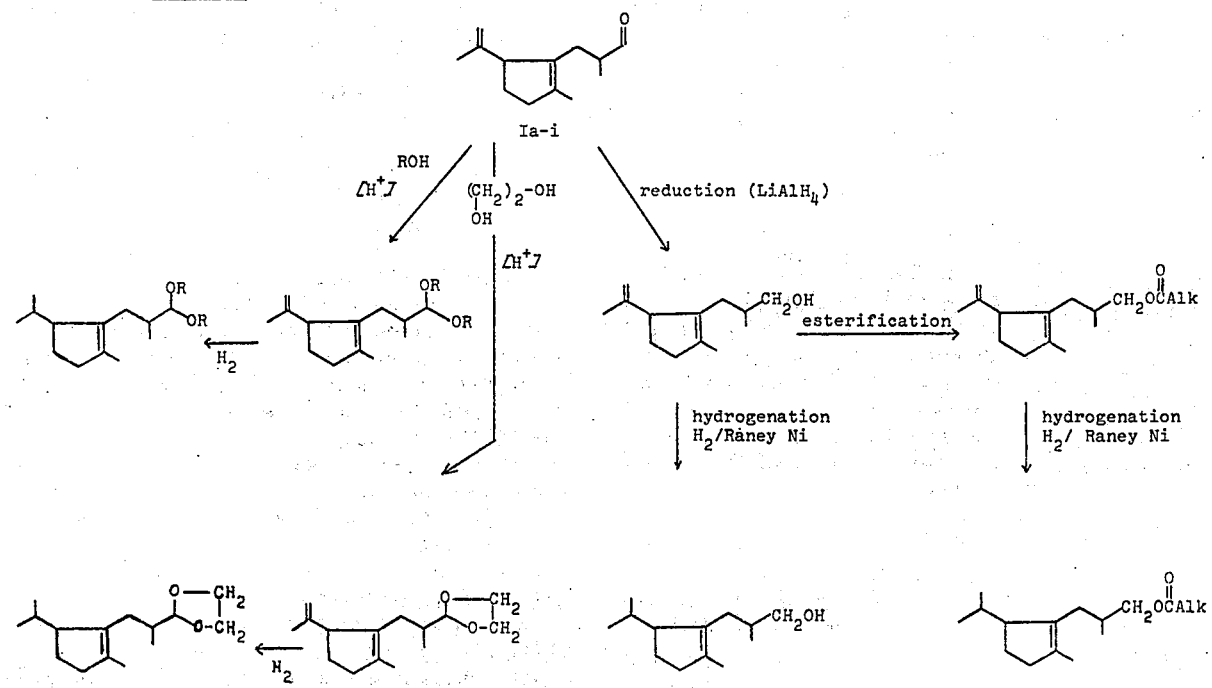

MS: M$^+$ = 152 (1); m/e = 137 (66); 119 (35); 109 (45); 91 (22); 79 (57); 67 (36); 55 (27); 43 (100); 27 (22).

b)
2-methyl-3-(2-methyl-5-isopropenyl-cyclopent-1-en-1-yl)-propanal i. Under Pressure 15.2 g of 1-methyl-2-methylene-3-isopropenyl-cylcopentan-1-ol, obtained according to letter a), 29.2 g of ethoxyprop-1-ene and 0.1 g of 85% phosphoric acid were warmed up under nitrogen of about 150° during about 60 minutes in a sealed tube.

The reaction mixture was then poured onto crushed ice and extracted with ether. After the usual treatments of washing, neutralization and drying, the combined organic extracts were evaporated and distilled to give 15.7 g of a product having bp. 55°–60°/0.1 Torr.

By redistillation there were obtained 13.5 g (yield 70%) of the desired aldehyde; $n_D$ = 1.4810; $D^{20}$ = 0.9147

IR: 3085, 2700, 1725, 1640, 878 cm$^{-1}$
NMR: 0.94 (3H, d, J=7 cps); 1.57 (3H, s); 1.69 (3H, s); 4.69 (m); 9,5 (1H, s, J=2 cps) δ ppm
MS: M$^+$ = 192 (43); m/e: 177 (17); 164 (60); 149 (63); 135 (26); 121 (98); 107 (72); 93 (100); 79 (61); 67 (25); 55 (48); 41 (80); 29 (32).

ii. At Atmospheric Pressure 228 g (1.5 Mole) of 1-methyl-2-methylene-3-isopropenylcyclopentan-1-ol, obtained according to letter a), 438 g (3 Mole) of ethoxy-prop-1-ene and 2 ml of 85% phosphoric acid were heated to the reflux temperature under nitrogen during approximately 48 hours (the temperature of the reaction mixture was of about 85°–90°).

The reaction mixture was then treated in accordance with the procedure given hereinabove (see paragraph i.). There were obtained 233 g of a product which upon fractional distillation gave 180 g of the desired aldehyde with a yield of 63 percent.

2-Methyl-3-(2-methyl-5isopropenyl-cyclopent-1-en-1-yl)-propanal (hereinafter referred to as: aldehyde A) can be used as a starting material for the preparation of:

2-methyl-3-(2-methyl-5-isopropenyl-cyclopent-1-en-1-yl)propanol 29 g of aldehyde A in 250 ml of ether were added dropwise to a suspension of 4 g of LiAlH$_4$ in 100 ml of ether and the whole was kept under stirring during 2 hours. The reaction mixture was then poured onto crushed ice and extracted with ether, whereupon the combined organic extracts, after the usual treatments of washing, neutralization and drying, gave on evaporation and subsequent distillation 28 g of the desired alcohol (yield 95 percent);

$n_D$ 32 1.4894; $d^{20}$ = 0.9198
IR: 3380, 1790, 1640, 885 cm$^{-1}$
MS: M$^+$ = 194 (40); m/e: 179 (7); 161 (16); 151 (40); 136 (25); 121 (100); 107 (60); 93 (88); 79 (50); 55 (45); 41 (60); 29 (20).

The alcohol thus obtained can be converted into its corresponding acetate as follows:

2-methyl-3-(2-methyl-5-isopropenyl-cyclopent-1-en-1-yl)propyl acetate:

5 g of acetyl chloride and 3 g of acetic anhydride were added dropwise to a mixture of 10 g of the alcohol obtained according to the process indicated hereinabove and 20 g of dimethylaniline. Said mixture was previously cooled and kept under nitrogen.

The reaction mixture was maintained under stirring during one night.

After the usual treatments of extraction and washing there were obtained 12 g (yield 98%) of the desired acetate.

$n_D$ = 1.4715; $d^{20}$ = 0.9376
IR: 3080, 1738, 1640, 890 cm$^{-1}$
MS: M$^+$ = 236 (40); m/e: 193 (2); 177 (8); 161 (72); 147 (26); 133 (50); 119 (72); 105 (48); 92 (60); 79 (30); 69 (18); 55 (33); 43 (100); 29 (15).

2-methyl-3-(2-methyl-5-isopropyl-cyclopent-1-en-1-yl)propanol 9.7 g of 2-methyl-3-(2-methyl-5-isopropenyl-cyclopent-1-en-1-yl)-propanol were catalytically hydrogenated in the presence of traces of Raney nickel in methanol. 1130 ml of hydrogen were absorbed and the reaction mixture was filtered, whereupon the clear filtrate was evaporated to give 9.2 g of 2-methyl-3-(2-methyl-5-isopropyl-cyclopent-1-en-1-yl)-propanol;

$n_D$ = 1.4789; $D^{20}$ = 0.9084;
IR: 3400 cm$^{-1}$
MS: M$^+$ = 196 (5); m/e: 153 (20); 135 (24); 121 (4); 107 (16); 95 (100); 79 (16); 69 (10); 55 (15); 41 (20); 29 (5).

The corresponding acetate was prepared in accordance with the method described hereinabove for the preparation of 2-methyl-3-(2-methyl-5-isopropenyl-cyclopent-1-en-1-yl)-propyl acetate.

$n_D$ = 1.4619; $d^{20}$ = 0.9264;
IR: 1740 cm$^{-1}$
MS; M$^+$ = 239 (4); m/e: 195 (8); 135 (100); 121 (2); 107 (22); 93 (60); 79 (18); 69 (5); 55 (12); 43 (40); 29 (4).

2-methyl-3-(2-methyl-5-isopropenyl-cyclopent-1-en-1-yl)propyl formate 10 g of the alcohol, obtained according to the process given above, were reacted overnight at room temperature in 50 ml of toluene, with 50 g of formic acid in the presence of 2.5 g of molecular sieves (3 A - pearl form, Merck). The toluenic phase was separated and washed with water and an aqueous solution of NaHCO$_3$ until neutrality, then dried over Na$_2$SO$_4$. Evaporation followed by fractional distillation gave 8.7 g (yield 76%) of pure formate;

$n_D$ = 1.4752; $d^{20}$ = 0.9495;
IR: 3080, 1805, 1725, 1640 and 890 cm$^{-1}$;
NMR: 0.8 and 0.91 (6H, 2d, J=7 cps); 1.53 (3H, s); 1.64 (3H, s); 3.88 (2H, m); 4.61 (2H, m) δ ppm
MS: M$^+$ = 222 (80); m/e: 207 (13), 161 (64), 133 (52), 121 (80), 93 (100), 79 (44), 55 (44), 41 (57).

2-methyl-3-(2-methyl-5-isopropyl-cyclopent-1-en-1-yl)propyl formate 10 g of the alcohol, obtained according to the process given above, were reacted with formic acid under the same reaction conditions as those given above. There were thus obtained 9.5 g of the desired ester:

bp. 90°–100°/0.01 Torr;
$n_D = 1.4669$; $d^{20} = 0.9361$;
IR: 1725 cm$^{-1}$;
NMR: 0.63 and 0.89 (6H, 1d each, J=7 cps): 1.6 (3H, s); 3.9 (2H, m) δ ppm
MS: M$^+$ = 224 (12); m/e: 181 (60), 135 (77), 107 (32), 93 (100), 79 (26), 67 (10), 55 (21), 41 (23), 29 (12).

2-methyl-3-(2-methyl-5-isopropenyl-cyclopent-1-en-1-yl)-propanal-dimethylketal 20 g of aldehyde A were heated to the reflux temperature during 2.5 hours in the presence of 0.2 g of p-toluenesulphonic acid in 200 ml of methanol. After evaporation of the volatile portions and extraction with ether of the obtained residue, the combined extracts were washed, neutralized by means of an aqueous solution of NaHCO$_3$ and dried. On evaporation of the ether and subsequent distillation there were obtained 18 g (yield 75%) of the desired ketal having bp. 58°–60°/0.2 Torr;
$n_D = 1.4738$; $d^{20} = 0.9309$;
IR: 3080, 1790, 1640, 1100, 888 cm$^{-1}$
MS: M$^+$ = 238 (0.1); m/e: 206 (36); 191 (8); 175 (24); 159 (48); 145 (35); 133 (17); 119 (40); 75 (100); 41 (30); 29 (10).

2-methyl-3-(2-methyl-5-isopropenyl-cyclopent-1-en-1-yl)-1-ethylenedioxy-propane 20 g of aldehyde A were heated to the reflux temperature during 3 hours in the presence of 0.3 g of p-toluenesulphonic acid and 7 g of ethylene glycol in a water separator. The mixture was then subjected to the same treatment as that indicated above for the preparation of the dimethylketal.

There were thus obtained 20 g (yield 80%) of the desired compound.

$n_D = 1.4870$; $d^{20} = 0.9738$;
IR: 3080, 1785, 1640, 1100, 885 cm$^{-1}$
MS: M$^+$ = 236 (12); m/e: 221 (0.1) 207 (0.1); 193 (1); 174 (9); 15 (25); 145 (20); 134 (7); 113 (32); 100 (52); 73 (100); 45 (30); 29 (10).

The ketals obtained as indicated hereinabove can then be subjected to a catalytic hydrogenation according to the method indicated above for the preparation of 2-methyl-3-(2-methyl-5-isopropyl-cyclopent-1-en-1-yl)-propanol.

2-Methyl-3-(2-methyl-5-isopropyl-cyclopent-1-en-1-yl)-propanal-dimethylketal was thus obtained;

$n_D = 1.4648$; $d^{20} = 0.9187$;
IR: 1100 cm$^{-1}$

MS: M$^+$ = 240 (0.1); m/e: 208 (26); 165 (65); 133 (100); 121 (26); 105 (25); 93 (32); 75 (65); 41 (30); 29 (20).

In the same way 2-methyl-3-(2-methyl-5-isopropyl-cyclopent-1-en-1-yl)-1-ethylenedioxypropane was obtained;

$n_D = 1.4789$; $d^{20} = 0.9596$;
MS: M$^+$ = 238 (15); m/e: 195 (46); 176 (1); 161 (7); 151 (4); 133 (60); 121 (15); 113 (70); 101 (60); 95 (100); 79 (20); 73 (62); 55 (20); 41 (34); 29 (34).

EXAMPLE 2

2-Methyl-3-(2-methyl-5-isopropyl-cyclopent-1-en-1-yl)-propanal 19.2 g (0.1 Mole) of 2-methyl-3-(2-methyl-5-isopropenyl-cyclopent-1-en-1-yl)-propanal in 100 ml of dioxan were reduced by catalytic hydrogenation in the presence of traces of palladium over charcoal. After absorption of 2300 ml of hydrogen (10 hours) the reaction mixture was filtered and the clear filtrate evaporated under reduced pressure. The obtained residue was then distilled to give 18.3 g of the desired aldehyde;

bp. 45°–50°/0.1 Torr;
$n_D = 1.4710$; $d^{20} = 0.9069$;
IR: 2700, 1730 cm$^{-1}$
NMR: 0.67–1.1 (several doublets); 1.66 (3H, s); 9.5-9.65 (1H, 2d, J=3 cps) δ ppm
MS: M$^+$ = 194 (22); m/e: 177 (0.1); 164 (1); 151 (50); 133 (28); 123 (98); 107 (18); 95 (88); 81 (100); 67 (30); 55 (33); 41 (50); 27 (22).

EXAMPLE 3

2-Methyl-3-(2-methyl-5-isopropyl-cyclopent-1-en-1-yl)-prop-2-enol 40 g of ethyl 2-methyl-3-(2-methyl-5-isopropyl-cyclopent-1-en-1-yl)-prop-2-enoate in 100 ml cooled ether were added under stirring to a suspension of 4 g of LiAlH$_4$ in 50 ml ether. After addition of water to the thus obtained suspension, the separated organic phase was dried and evaporated to dryness. There was thus obtained 31.4 g (yield 95%) of the desired alcohol; bp. 75°–80°/0.01 Torr.

An analytical sample was prepared by purification via vpc;

$n_D = 1.5030$; $d^{20} = 0.9367$; $[\alpha]_D = +169°$
IR: 3400 cm$^{-1}$;
NMR: 0.66 and 0.87 (6H, 1d each, J= ca. 7 cps); 1.58 and 1.6 (6H, 2s); 3.95 (2H, m); 5.72 (1H, m) δ ppm
MS: M$^+$ = 194 (28); m/e: 176 (2), 151 (100), 133 (40), 123 (20), 105 (30), 93 (72), 81 (60).

The corresponding acetate was prepared in accordance with the techniques conventional in the art by treating the alcohol with acetyl chloride. The obtained ester showed the following analytical data:

$n_D = 1.4839$; $d^{20} = 0.9545$; $[\alpha]_D = +145°$;
IR: 1740 cm$^{-1}$
NMR: 0.65 and 0.86 (6H, 1d each, J= ca. 6 cps); 1.56 or 1.57 (6H, 1s each); 4.42 (2H, m); 5.7 (1H, m) δ ppm MS: M$^+$ = 236 (5); m/e: 193 (15); 176 (7); 161 (3); 133 (100); 119 (8); 105 (25), 91 (20), 43 (55).

The corresponding aldehyde, 2-methyl-3-(2-methyl-5-isopropyl-cyclopent-1-en-1-yl)-prop-2-enal, was synthetized by oxidizing by means of MnO$_2$ the alcohol obtained above according to conventional techniques. The aldehyde showed the following analytical data:

$n_D$ = 1.5319; $d^{20}$ = 0.9419; $[\alpha]_D$ = +532°;
IR: 2690, 1690 and 1620 cm$^{-1}$
NMR: 0.68 and 0.91 (6H, 1d each, J=7 cps); 1.73 (6H, 2s); 6.72 (1H, m); 9.4 (1H, s) δ ppm
MS: M$^+$ = 192 (10); m/e: 177 (20), 149 (100), 131 (15), 121 (18), 93 (25), 79 (15), 43 (15).

Ethyl 2-methyl-3-(2-methyl-5-isopropyl-cyclopent-1-en-1-yl)-prop-2-enoate, used as starting material in the hereinabove preparation, can be synthetized by the following procedure:

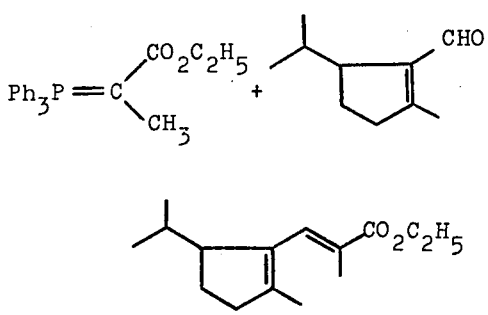

15.2 (0.1 Mole) of the aldehyde prepared in accordance with Compt. Rend. 254, 1087 (1962), in 1 lt of benzene were reacted at reflux temperature under the usual reaction conditions required for the Wittig reaction with 80 g of the phosphorane obtained from triphenyl-phosphine and ethyl α-bromopropionate [prepared according to Helv. Chim. Acta 40, 1248 (1957)].

There was thus obtained the desired ester (16 g; yield 70%);

$n_D$ = 1.4991; $d^{20}$ = 0.9707; $[\alpha]_D$ = + 264°;
IR: 1710, 1640 and 1630 cm$^{-1}$;
NMR: 0.68 and 0.89 (6H, 1d each, J= ca. 7 cps); 1.3 (3H, t, J=7 cps); 4.18 (2H, q, J= ca. 6 cps); 7.03 (1H, m) δ ppm
MS: M$^+$ = 236 (13); m/e: 221 (1), 193 (92), 147 (100), 119 (65), 91 (20), 41 (18).

EXAMPLE 4

"Eau de toilette" for Men

A base perfume composition of the type "eau de toilette" for men was prepared by mixing the following ingredients (parts by weight):

| | |
|---|---|
| Synthetic bergamot oil | 250 |
| Vetyveryl acetate | 150 |
| Cedryl acetate | 100 |
| Lavender oil 40–45 % | 60 |
| Lemon oil | 50 |
| Synthetic leather | 40 |
| Galbanum resinoid | 30 |
| Hydroxycitronellal | 30 |
| Rosmarin oil of Spain | 30 |
| Synthetic neroli | 20 |
| Geranium Bourbon oil | 20 |
| Coumarin | 20 |
| Nutmeg oil | 15 |
| Camomile oil of Morocco | 10 |
| Abs. oak moss | 10 |
| Tobacco resinoid 10 %* | 10 |
| Artemisian oil | 5 |
| Isobornyl acetate | 10 |
| 1,6,10,10-tetramethyl-2-oxa-tricyclo[8.3.0.0$^{6,11}$]tridecane 0.1 %* | 20 |
| Citronellol | 20 |
| Diethyl phthalate | 100 |
| Total | 1000 |

*in diethyl phthalate

By adding to 900 ml of the above composition 100 ml of 2-methyl-3-(2-methyl-5-isopropyl-cyclopent-1-en-1-yl)-propanal there was obtained a new perfume composition possessing a dry, herbaceous note which was reminiscent of the olfactive character of marjoram.

EXAMPLE 5

Herbs shampoo

A perfume composition for herbs shampoo was prepared by admixing the following ingredients (parts by weight);

| | |
|---|---|
| Terpenyl acetate | 100 |
| Cedar oil of Florida | 100 |
| Synthetic bergamot oil | 80 |
| Concrete "mousse d'arbre" 50 %* | 60 |
| Amyl salicylate | 60 |
| Coumarin | 60 |
| 1,1-dimethyl-4-acetyl-6-ter-butylindane 10 %* | 50 |
| Galbanum resinoid | 40 |
| Cedryl acetate | 40 |
| Synthetic citronellol | 40 |
| Natural geraniol | 40 |
| Synthetic lavandin oil | 40 |
| Eugenol | 30 |
| Geranyl acetate | 30 |
| Synthetic geranium Bourbon | 30 |
| Patchouli oil | 25 |
| Ambrette musk | 20 |
| Aspic oil | 15 |
| Synthetic neroli | 15 |
| Methylnonylacetic aldyhde 10 %* | 15 |
| Synthetic civet | 10 |
| Thuyopsanone | 10 |
| Benjoin resinoid of Siam 50 %* | 10 |
| Diethyl phthalate | 80 |
| Total | 1000 |

*in diethyl phthalate

By adding to 900 ml of the perfume composition obtained above 100 ml of 2-methyl-3-(2-methyl-5-isopropyl-cyclopent-1-en-1-yl)-propanal there was obtained a new composition possessing an herbaceous, fresh, minty note which was reminiscent of the olfactive note of marjoram.

By substituting 2-methyl-3-(2-methyl-5-isopropenyl-cyclopent-1-en-1-yl)-propanal for the mentioned aldehyde analogous effects were observed although in a less pronounced way.

EXAMPLE 6

Maritime Pine

A basic perfume composition of "maritime pine" type was prepared by admixing the following ingredients (parts by weight):

| | |
|---|---|
| Isobornyl acetate | 300 |
| Methylnonylacetic aldehyde 10 %* | 150 |
| Pine oil of Siberia | 150 |
| Terpenyl acetate | 150 |
| Pine oil of Canada | 100 |
| Neryl acetate | 50 |
| Cedar leaves oil | 30 |
| Galbanum resinoid | 20 |

-continued

| | |
|---|---|
| Dodecanoic aldhyde 10 %* | 10 |
| Diethyl phthalate | 40 |
| Total | 1000 |

*in diethyl phthalate

By adding to 960 ml of the above composition 40 ml of 2-methyl-3-(2-methyl-5-isopropenyl-cyclopent-1-en-1-yl)-propanal there was obtained a new composition which possessed an odoriferous note of pine which was more pronounced than that shown by the basic composition. The note was reminiscent of that shown by maritime pines.

EXAMPLE 7

Flavouring Composition of the "Tutti-Frutti" Type

A flavouring composition of the "tutti-frutti" type was prepared by admixing the following ingredients (parts by weight):

| | |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 400 |
| Total | 975 |

25 g of 2-methyl-3-(2-methyl-5-isopropyl-cyclopent-1-en-1-yl)-propanal were added to 975 g of the above mixture which was then called "test" composition A "control" composition was prepared by adding 25 g of additional lemon oil to 975 g of the above mixture.

The test and the control compositions were added to the foodstuffs described hereinafter in the proportions shown for 100 kg of material to be flavoured.

| | |
|---|---|
| Cake | 20 g |
| Pudding | 5 - 10 g |
| Toffee | 15 - 20 g |

Toffee:
100 ml of sugar sirup (prepared by dissolving 1 kg of sucrose in 600 ml of water) and 20 g of glucose were mixed together and slowly heated to 145°. The flavour was added and the mass was allowed to cool and harden.

Pudding:
To 500 ml of warm milk there was added a mixture of 60 g of sucrose and 3 g of pectin. The mixture was boiled for a few seconds and the flavour was added. The mixture was then allowed to cool.

Cake:
The following ingredients were mixed together: 100 g of vegetable margarine, 1.5 g. of sodium chloride, 100 g of sucrose, 2 eggs and 100 g of flour. The flavour was added and the mass was cooked for 40 minutes at 180°.

The finished foodstuff samples were tested by a panel of trained persons who had to express their views about the flavour of the said samples. All members of the panel declared that the test samples had a more fruity note than the control samples and at the same time a melon character.

Analagous results were observed by substituting in the above example 2-methyl-3-(2-methyl-5-isopropenyl-cyclopent-1-en-1-yl)-propanal for 2-methyl-3-(2-methyl-5-isopropylcyclopent-1-en-1-yl)-propanal. However, in this case the fruity note was paralleled by a flowery note reminiscent of cucumber.

EXAMPLE 8

1 g of a 0.01% alcoholic solution, in 95% ethanol, of 2-methyl-3-(2-methyl-5-isopropenyl-cyclopent-1-en-1-yl)-propyl acetate was added to 200 g of commercial mulberry jam possessing a bland taste. The thus flavoured jam was checked against a control jam obtained by mixing 1 g of 95% ethanol with 200 g of the commercial mulberry jam.

A panel of experts found that the flavoured jam possessed a slightly musky-woody note typical of fresh mulberry fruits.

EXAMPLE 9

1 g of a 0.01% alcoholic solution, in 95% ethanol, of 2-methyl-3-(2-methyl-5-isopropenyl-cyclopent-1-en-1-yl)-propyl acetate was added to 500 g of a commercially available vodka liquor. The thus flavoured beverage was checked against a control liquor obtained by adding to 500 g of the commercial vodka, 1 g of 95% ethanol.

The panel of experts found that the flavoured liquor possessed a richer note with a better lifting than the unflavoured material. The note developed was reminiscent of the musky character of British gin.

EXAMPLE 10

After-shave Lotion

An after-shave lotion composition was prepared by mixing the following ingredients (parts by weight):

| | |
|---|---|
| Galbanum oil 10 %* | 120 |
| Bergamot (synth.) | 100 |
| p-ter-Butyl-cyclohexanyl acetate | 100 |
| Cedryl acetate | 100 |
| Methyl-octyl acetaldehyde 10 %* | 80 |
| Synth. Jasmin oil | 60 |
| Lemon oil | 60 |
| Colourless oak moss abs. 50 %* | 50 |
| Lavandin oil | 50 |
| Clove oil of Madagascar | 40 |
| Synth. Neroli | 40 |
| Dimethyl-cyclohexene-carbaldehyde 10 %* | 40 |
| Concentrated orange oil (Tetrarome, Firmenich SA) | 30 |
| Dodecanal 10 %* | 30 |
| Stryallyl acetate | 30 |
| Patchouli oil | 20 |
| Sandela, Givaudan & Cie. S.A. | 10 |
| α-Iso-methylionone | 10 |
| 1,1-Dimethyl-4-acetyl-6-ter-butyl-indane | 10 |
| Total | 980 |

*in diethyl phthalate

By adding to 900 g of the above given composition 100 g of 2-methyl-3-(2-methyl-5-isopropenyl-cyclopent-1-en-1-yl)-propyl acetate there was obtained a new composition which possessed an improved richness when compared with the basic composition. The olfactive note was more harmonious with a typical character of woody-powdery sandelwood odour.

EXAMPLE 11

Chypre Type Composition

A base perfume composition of the chypre type was prepared by mixing the following ingredients (parts by weight):

| | |
|---|---:|
| Synth. jasmin abs. | 220 |
| Oak moss abs. 10 %* | 180 |
| α-Iso-methylionone | 110 |
| Coumarin | 100 |
| Methyl di- and tetrahydro-abietate | 80 |
| Opoponax oil 10 %* | 50 |
| Synth. rose oil | 50 |
| Oriental sandelwood oil | 50 |
| Undecalactone | 40 |
| Patchouli oil | 40 |
| Eugenol extra | 30 |
| Carrot seeds oil 1 %* | 40 |
| Benjoin resinoid of Siam 50 %* | 10 |
| Total | 1000 |

*in diethyl phthalate

By adding to 900 g of the above given composition 100 g of 2-methyl-3-(2-methyl-5-isopropenyl-cyclopent-1-en-1-yl)-propyl acetate there was obtained a new composition which possessed an improved richness and a more developed harmonious powdery character. The olfactive note of the new composition was more "ambrette seeds" like.

EXAMPLE 12

Perfumed Soap

A base perfume composition was prepared by mixing together 80 parts by weight of a commercial "Fougere" type composition and 10 parts by weight of western sandelwood oil with 10 parts by weight of sandelwood oil Mysore.

A test perfume composition was prepared by mixing 80 parts by weight of a commercial "Fougere" type composition and 10 parts by weight of western sandelwood oil with 10 parts by weight of 2-methyl-3-(2-methyl-5-isopropenyl-cyclopent-1-en-1-yl)-propyl acetate. The said base and test compositions were separately added in the proportion of 1% by weight, based on the finished product, to a non-perfumed commercial soap paste.

The paste was treated according to the usual techniques in order to obtain toilet soaps.

The soap perfumed with the test composition possessed a fragrance having a rounder character than that of the soap perfumed by the base composition. The former possessed moreover a well defined woody character which was in all respects identical with that of the soap perfumed by the base composition.

What is claimed is:

1. Compounds of formula

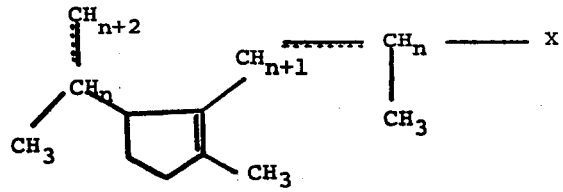

containing a single or a double bond in the positions indicated by the dotted lines and wherein:

n stands for 0 or 1; and X represents a univalent radical of formula
$-CH_2OR^1$
wherein $R^1$ represents a hydrogen atom or an acyl radical derived from a fatty acid containing from 1 to 6 carbon atoms.

2. 2-Methyl-3-(2-methyl-5-isopropenyl-cyclopent-1-en-1-yl)-propanol.

3. 2-Methyl-3-(2-methyl-5-isopropenyl-cyclopent-1-en-1-yl)-propyl acetate.

4. 2-Methyl-3-(2-methyl-5-isopropyl-cyclopent-1-en-1-yl)-propanol.

5. 2-Methyl-3-(2-methyl-5-isopropyl-cyclopent-1-en-1-yl)-propyl acetate.

6. 2-Methyl-3-(2-methyl-5-isopropenyl-cyclopent-1-en-1-yl)-propyl formate.

7. 2-Methyl-3-(2-methyl-5-isopropyl-cyclopent-1-en-1-yl)-propyl formate.

8. 2-Methyl-3-(2-methyl-5-isopropyl-cyclopent-1-en-1-yl)-prop-2-enol.

9. 2-Methyl-3-(2-methyl-5-isopropyl-cyclopent-1-en-1-yl)-prop-2-enyl acetate.

* * * * *

UNITED STATES PATENT AND TRADEMARK OFFICE
CERTIFICATE OF CORRECTION

PATENT NO. : 3,937,723
DATED : February 10, 1976
INVENTOR(S) : Karl-Heinrich Schulte-Elte It is certified that error appears in the above-identified patent and that said Letters Patent are hereby corrected as shown below:

Column 1, line 22 "Oor" should be--zero or--

Column 1, line 24 "(b)-CH-OR; OR" should be--
$$(b)-\underset{\underset{OR}{|}}{C}H-OR \ ;$$

Column 1, line 25 "(d)-CH-O O-$(CH_2)_2$" should be--

$$(d)-\underset{\underset{O-(CH_2)_2}{|}}{C}H-\underset{|}{O}$$ --

Column 2, line 11 "such a" should be--such as  --

Column 3, line 9 "len" should be--1-en--

Column 3, line 21 "5isopropyl" should be--5-isopropenyl--

Column 3, line 42 "isopropenylcyclopent" should be--
    isopropenyl-cyclopent--

Column 7, line 43 "5isopropyl" should be--5-isopropenyl--

Column 7, line 61 "$n_D$ 32 1.4894" should be--$n_D$ = 1.4894--

Column 8, line 2 "yl)propyl" should be--yl)-propyl--

Column 8, line 19 "92" should be--93--

Column 8, line 51 "yl)propyl" should be--yl)-propyl--

UNITED STATES PATENT AND TRADEMARK OFFICE
CERTIFICATE OF CORRECTION

PATENT NO. : 3,937,723

DATED : February 10, 1976

INVENTOR(S) : Karl-Heinrich Schulte-Elte

It is certified that error appears in the above-identified patent and that said Letters Patent are hereby corrected as shown below:

Column 9, line 2, "yl)propyl" should be --yl)-propyl--

Column 13, line 32 "composition A" should be --composition. A--

Column 14, line 10 "control" should be --"control"--

Column 14, line 23 "control" should be --"control"--

Signed and Sealed this

Fifteenth Day of February 1977

[SEAL]

Attest:

RUTH C. MASON
Attesting Officer

C. MARSHALL DANN
Commissioner of Patents and Trademarks